(12) United States Patent
Kwong

(10) Patent No.: US 6,786,724 B1
(45) Date of Patent: Sep. 7, 2004

(54) MOLD COMPOUND EJECTION TIP FOR DENTISTRY

(76) Inventor: William K. Kwong, 36 Oak Rd., Orinda, CA (US) 94563

( * ) Notice: Subject to any disclaimer, the term of this patent is extended or adjusted under 35 U.S.C. 154(b) by 141 days.

(21) Appl. No.: 10/158,427

(22) Filed: May 29, 2002

(51) Int. Cl.[7] ................................................. A61C 5/04
(52) U.S. Cl. ........................................ 433/90; 222/575
(58) Field of Search .............................. 433/48, 89, 90, 433/214; 222/575

(56) References Cited

U.S. PATENT DOCUMENTS

| | | | | |
|---|---|---|---|---|
| 2,664,088 A | * | 12/1953 | Hoch | |
| 3,109,427 A | * | 11/1963 | Davidson | |
| 4,768,954 A | * | 9/1988 | Dragan | 433/90 |
| 5,244,388 A | * | 9/1993 | Frush | 433/90 |
| 5,743,436 A | * | 4/1998 | Wilcox et al. | 222/137 |
| 6,007,335 A | * | 12/1999 | Sheu | 433/90 |
| 6,065,651 A | * | 5/2000 | Tedeschi, Jr. et al. | 222/519 |

OTHER PUBLICATIONS

Figure 1 and Figure 2 of U.S. patent application No. 10/158,427, filed May 29, 2002.

* cited by examiner

*Primary Examiner*—Cary E. O'Connor
(74) *Attorney, Agent, or Firm*—William Michael Hynes; Townsend and Towsend and Crew LLP

(57) ABSTRACT

An intra-oral molding compound ejection tip is provided to provide a substantially uniform expanding solid angle of the mixed molding compound upon molding compound ejection. A prior art intra-oral tip typically includes an ejection orifice defined about an axis parallel to the direction of mold compound ejection. In a preferred embodiment, two cuts are placed in the tip at right angles to one another within the plane of the normal axis of molding compound ejection. Each of these cuts is sized with respect to the ejection orifice to produce a uniformly expanding solid angle of the ejected molding compound. This uniformly expanding solid angle of the ejected molding compound has the property of having higher normal incidence to both preparation and margin to the preparation in teeth having dental surgery.

7 Claims, 4 Drawing Sheets

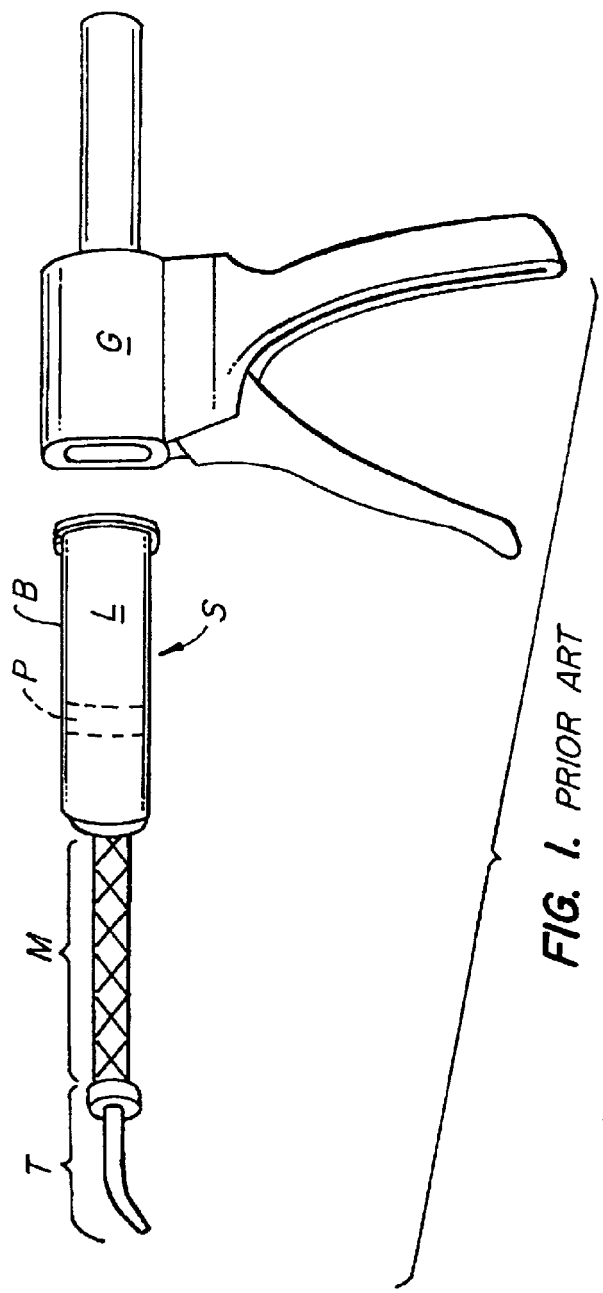
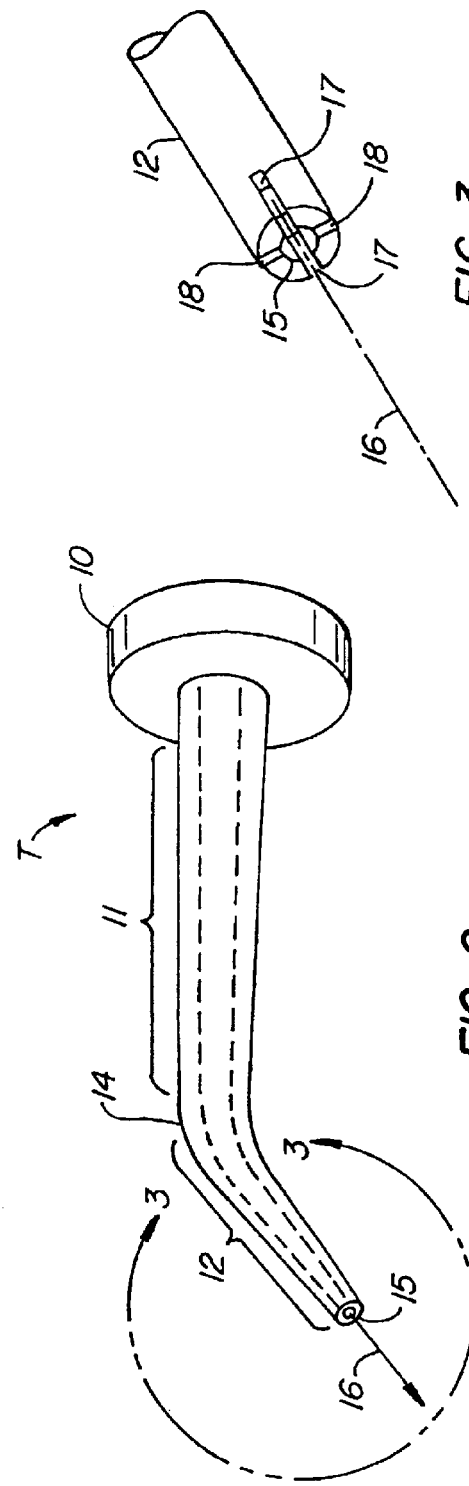
FIG. 1. PRIOR ART
FIG. 2. PRIOR ART
FIG. 3.

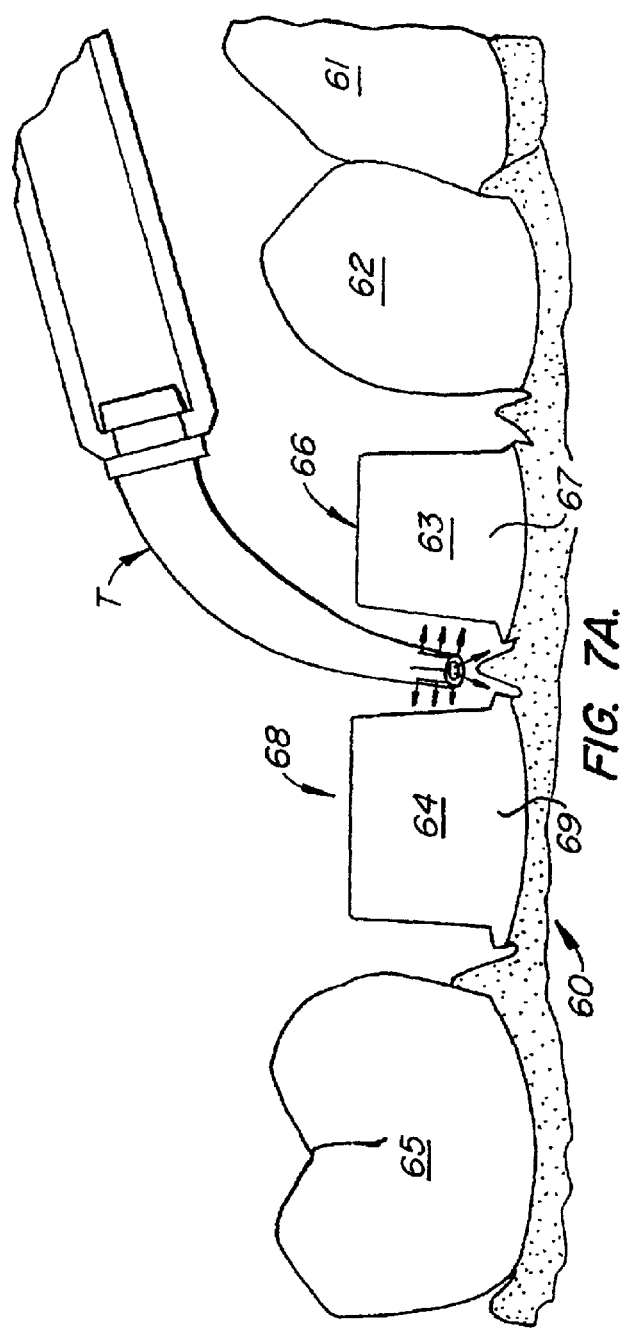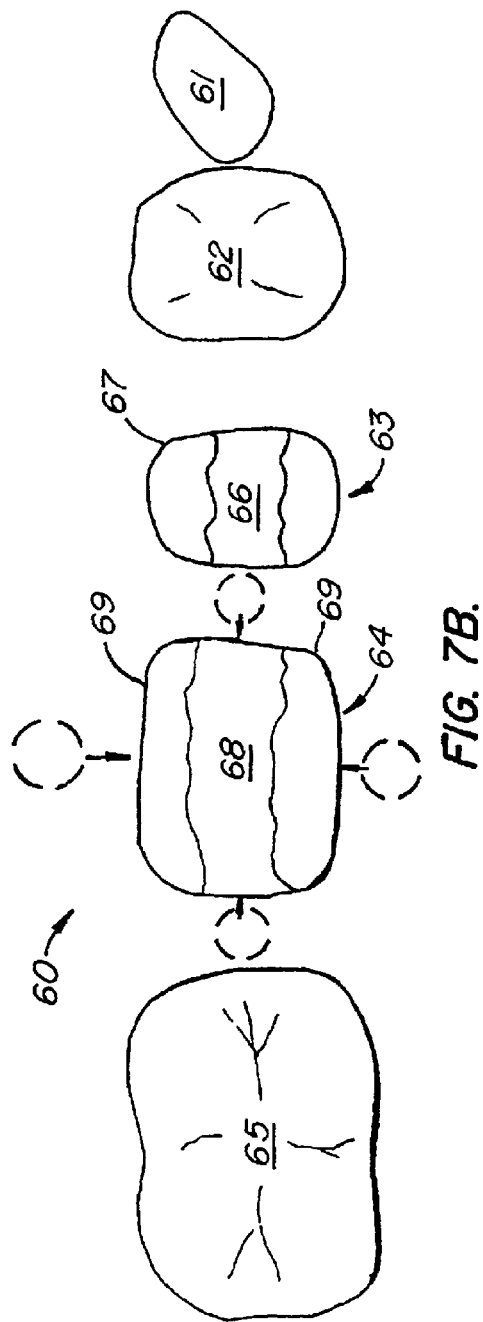
FIG. 7A.
FIG. 7B.

MOLD COMPOUND EJECTION TIP FOR DENTISTRY

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

This invention relates to the ejection of freshly mixed mold compound to teeth having completed dental surgery preparations. More particularly, a nozzle which ejects recently mixed and curing molding compound is ejected along a uniformly expanding solid angle for overcoming wetting-resistant surface tension between the molding compound and prepared teeth.

BACKGROUND OF THE INVENTION

This invention relates to the molding step of dental surgery. To understand the molding step, it is necessary to briefly review the dentistry in which the molding step is practiced. Accordingly, a simplified summary of dentistry resulting in placement of a crown to a tooth follows.

Decay is surgically removed from a tooth or teeth, and a preparation made to receive a crown. A mold of the preparation and margin adjacent to the preparation is made in order to construct a model. Once the mold of the preparation is made, the patient receives a temporary filling and leaves the dental office.

With the patient absent, a model of the tooth or teeth is constructed. The crown is then made to fit the model of the preparation. Presuming that the model of the preparation is an exact replication of the tooth with the preparation, the prepared crown will precisely fit the surgically altered tooth of the patient. When the patient returns to the dentist's office, the crown is first fitted to and thereafter adhered to the preparation. Reconstructive dental surgery results.

Accurate molding is extraordinarily important in this process. Unfortunately, dental preparations by their very nature are a less than optimal environment for accurate molding. Where an inaccurate mold is made, the resultant crown cannot be used. When this occurs, a new mold must be made, a new model of the tooth or teeth fabricated, a new crown constructed, and the patient asked to return at a later time to the dental office for adhering the crown to the preparation.

Molding compound is generated from an elongate syringe-like appliance having thumb depressed plungers evacuating side-by-side cylinders of base and catalyst. Paired thumb depressed plungers simultaneously eject approximately equal amounts of base and catalyst to a static mixer attached to the appliance. The static mixer mixes the base and catalyst into a mixture. As soon as the mixture is made, curing of the molding compound begins. When the molding compound is fully cured around a tooth having a preparation, a female silicone rubber mold results from which the male model of the tooth or teeth can be constructed.

Immediately before leaving the syringe-like appliance, the freshly mixed molding compound passes from the static mixer to an intra-oral tip. The intra-oral tip is typically disposed at an angle with respect to the syringe-like appliance. This tip directs the curing molding compound onto the preparation and surrounding teeth to make the mold.

The deposit of the molding compound to the surgically altered tooth at the preparation and the margin around the preparation (those portions of the tooth which have not been surgically altered) is difficult. Dentists try to direct molding compound onto the preparation and tooth margin surrounding the preparation by manipulation of the syringe-like mold mixing apparatus. These manipulations are made so that the molding compound can wet both the tooth surface and preparation interior of the tooth in order to create an accurate mold. Unfortunately, at least three factors restrict this maneuverability.

Simply stated, the mouth of the patient, which is usually being held in an (uncomfortable) open position, restricts mold mixing tool manipulation. The syringe-like appliance as maneuvered by the dentist is restricted in motion by the confines of the patient's mouth. Secondly, the location of the surgically repaired tooth can further restrict mold mixing tool manipulation. The immediately surrounding gums, cheek, teeth and mouth structure to the surgically altered tooth further restricts manipulation of the syringe-like mold compound mixing tool. Finally, the location of the preparation on the tooth can also restrict manipulation of the mold mixing tool. For example, where the preparation is on the back side of the tooth, the injection of freshly mixed and curing molding compound can be exceedingly difficult.

I have discovered that where molding compound is not directed normally to either a preparation surface or a tooth surface, the likelihood of an imperfectly generated mold having voids increases dramatically. I attribute this to surface tension which the surface of the tooth or preparation naturally has because of the wetting of the molding compound. Where normal contact is not made, the surface tension is not broken and voids in the mold can result.

A solution to this discovered problem was not immediately apparent. Specifically, preparations in teeth and adjacent tooth surfaces are frequently at large angles one to another. Where molding compound is directed normally on one surface—say a surface of the preparation—the molding compound can be directed substantially tangent to the preparation margin. Undesired voids can result.

The reader will understand that the discovery of a problem to be solved, as well as the solution to the problem, can constitute invention. Insofar as the problem which I have set forth relating to the wetting of teeth and preparations is not set forth in the prior art, I claim invention.

BRIEF SUMMARY OF THE INVENTION

An intra-oral molding compound ejection tip is provided to provide a substantially uniform expanding solid angle of the mixed molding compound upon molding compound ejection. A prior art intra-oral tip typically includes an ejection orifice defined about an axis parallel to the direction of mold compound ejection. In a preferred embodiment, two cuts are placed in the tip at right angles to one another within the plane of the normal axis of molding compound ejection. Each of these cuts is sized with respect to the ejection orifice to produce a uniformly expanding solid angle of the ejected molding compound. This uniformly expanding solid angle of the ejected molding compound has the property of having higher normal incidence to both preparation and margin to the preparation in teeth having dental surgery. An intra-oral tip having three slits, each at 120 degree angles about the normal axis of molding compound ejection will suffice for the practice of my invention. More generally, any combination of orifices which causes molding compound to expand from a point on the intra-oral tip along a uniformly expanding solid angle of expansion exceeding one pi steradian will suffice for the practice of this invention with the preferred ejection solid angle being a hemisphere or two pi steradians. In operation, the intra-oral tip is given excursion relative to a tooth with a preparation and margin surrounding the preparation with a portion of the solid angle of molding compound ejection preferably always directed normal to a tooth or preparation surface. Improved molding compound wetting occurs.

BRIEF DESCRIPTION OF THE DRAWINGS

FIG. 1 is a prior art view of the syringe-like molding compound ejection tool commonly used by dentists for the ejection of molding compound to a tooth or teeth having a preparation for molding the preparation and surrounding tooth at the margin;

FIG. 2 is a prior art view of an intra-oral molding compound ejection tip of the prior art illustrating the normal axis of molding compound ejection;

FIG. 3 is the intra-oral molding compound ejection tip of FIG. 2 with paired slits cut at 90 degree intervals along the normal axis of molding compound ejection;

DETAILED DESCRIPTION OF THE INVENTION

Figure 4:
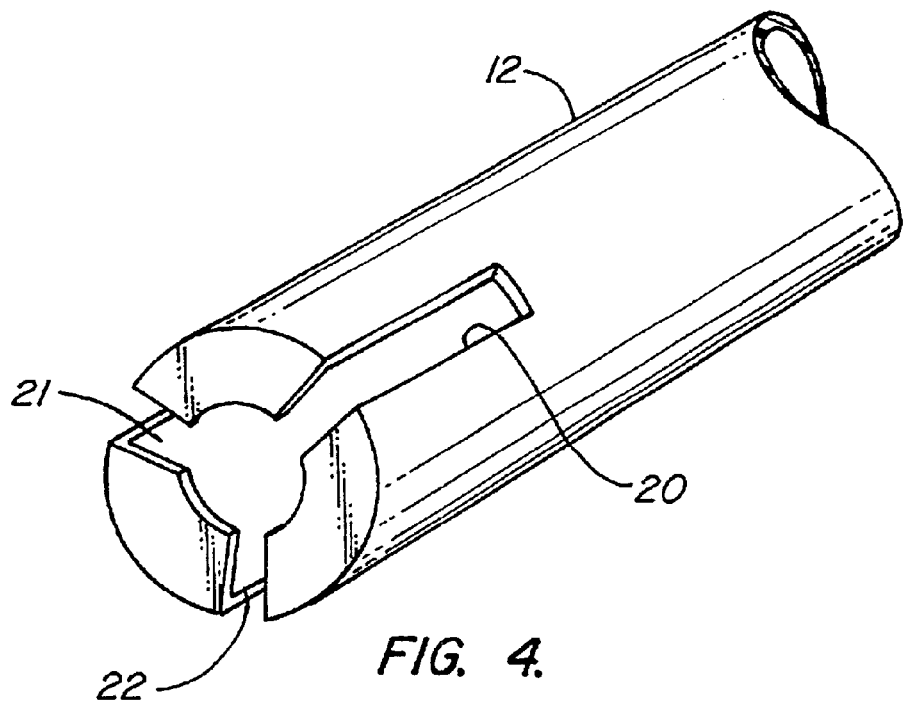
FIG. 4 is the intra-oral molding compound ejection tip of FIG. 2 with three slits cut at 120 degree intervals about the normal axis of molding compound ejection.

Referring to FIG. 1, mixer gun G is shown with mold mixing cylinders S in exploded relation with respect to the gun. Side-by-side catalyst cylinder L and base cylinder B are urged by piston P to and toward static mixer M for thorough mixing of the base and catalyst. An intra-oral tip T is shown attached at the end of the static mixer. The intra-oral tip, the subject of this invention, is shown in more detail in FIG. 2.

Referring to FIG. 2, static mixer attachment flange 10 has tip extension 11, tip bend 14 and tip exit extension 12 extending from the flange 10. Tip exit extension 12 includes a tip ejection aperture 15. Extending from tip ejection aperture 15 to flange 10 there is a continuous conduit (shown in broken lines) for ejecting mixed molding compound. Normally, and without this invention, mixed molding compound is ejected along the normal axis of mixed molding compound ejection 16.

Referring briefly to FIGS. 7A and 7B, and remembering that I have found preferable to have mixed molding compound normally incident to teeth such as first molar 64 at preparation 68 and margin 69, it will be realized that considerable (and impossible) manipulation of the mold mixing compound apparatus illustrated in FIG. 1 would have to occur as molding compound is placed the first premolar 64. Such movement would be restricted by the mouth of the patient, the preparation 68, the margin 69 and the adjacent mouth structure.

Referring to FIG. 3, the placement of the present invention is illustrated at tip exit extension 12. Tip ejection aperture 15 has two slits made along the plane including the normal axis of mixed molding compound ejection 16. First slits 17 are at right angles to second slits 18. The depth of the slits, when compared to the ejection aperture 15, and the widths of the slits, can all be empirically determined by those having skill in the art depending on the viscosity of mold mixing compound as it leaves static mixer M.

To produce a tip with an approximate hemispherical solid angle of molding compound ejection, when the external diameter of the tip is 1.8 mm and the ejection aperture is 0.8 mm, the wall thickness is 0.5 mm, and slit width is 0.2 mm with the depth being approximately 1 mm. The reader will understand that such tips come in various sizes. Other dimensions, all within the scope of the invention, can be easily determined by those having skill in the art.

Referring to FIG. 4, another embodiment molds such a tip at exit extension 12 with first slit 20, second slit 21 and third slit 22 all at 120 degree angles. This construction is not preferred.

Figure 5:
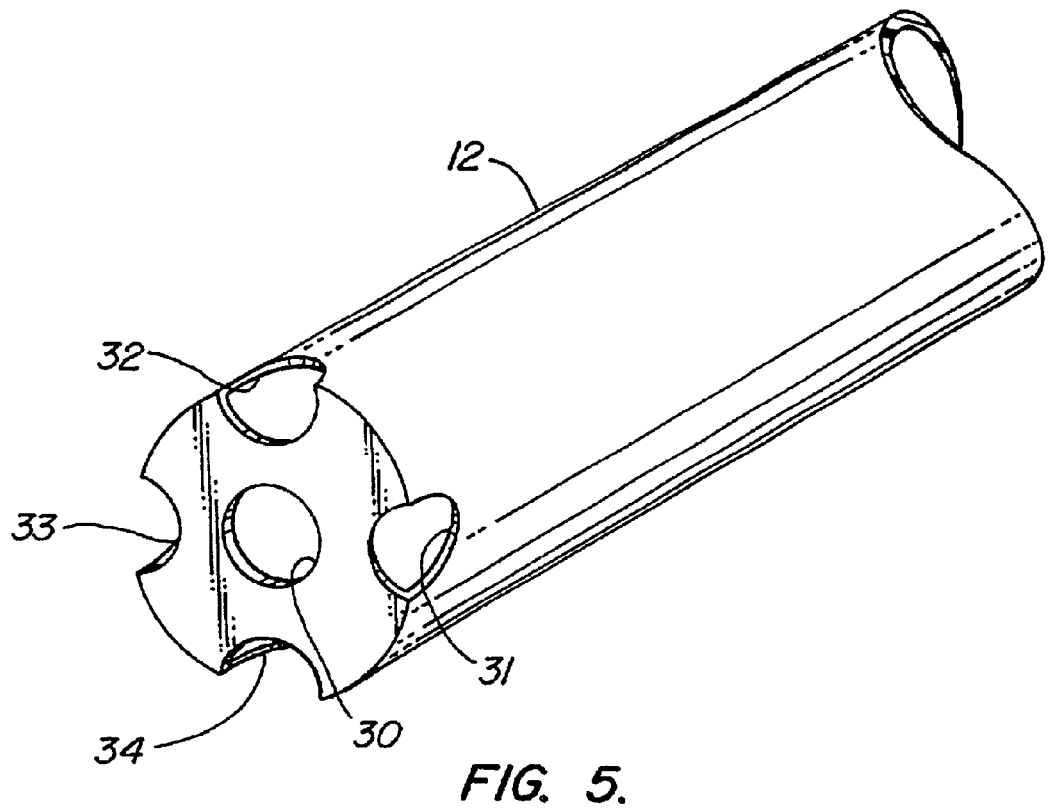
FIG. 5 is a tip having multiple orifices for ejecting molding compound advancing uniformly with respect to a solid angle of ejection.

Referring to FIG. 5, still another embodiment molds such a tip with discrete apertures. For example, exit tip extension 12 is shown having a central ejection aperture 30 with four side ejection apertures 31 to 34, all these apertures being at 90 degree intervals about the end of the tip.

Figure 6A:
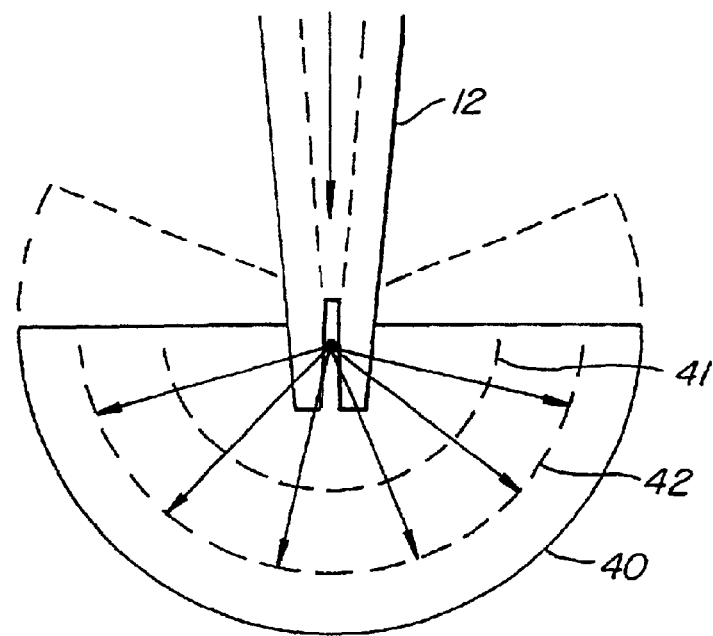
FIGS. 6A and 6B are respective illustrations a tip manufactured according to this invention with FIG. 6A illustrating expansion along a hemispheric solid angle and FIG. 6B illustrating expansion along a solid angle less than a hemisphere; and, FIGS. 7A and 7B are illustrations of side-by-side teeth having side-by-side preparations, illustrating in broken lines an excursion path for placement of molding compound for total wetting of the preparation and peripheral margin of the teeth.

Referring to FIG. 6A, tip exit extension 12 such as that illustrated in FIG. 3 is shown ejecting molding compound along a hemispherical molding compound front 40. It will be understood that as molding compound is ejected, the mixed molding compound successively expands through first expansion front 41, second expansion front 42, and finally to the illustrated hemispherical molding compound front 40. Due to the dimensions involved, only a theoretical explanation is presented for the observed expansion phenomena. Simply stated, it is believed that the viscosity of mixed molding compound produces a back pressure against complete forward movement of the molding compound. This causes expansion in all four directions to the side of the normal axis through the slits 17 and 18 of mixed molding compound ejection.

The illustrated ejection of molding compound in a hemispherical front having two pi steradians from the ejection aperture of exit extension 12 is preferred. The reader will understand that the hemispherical ejection could slightly exceed this solid angle as illustrated in broken lines in FIG. 6A.

Figure 6B:
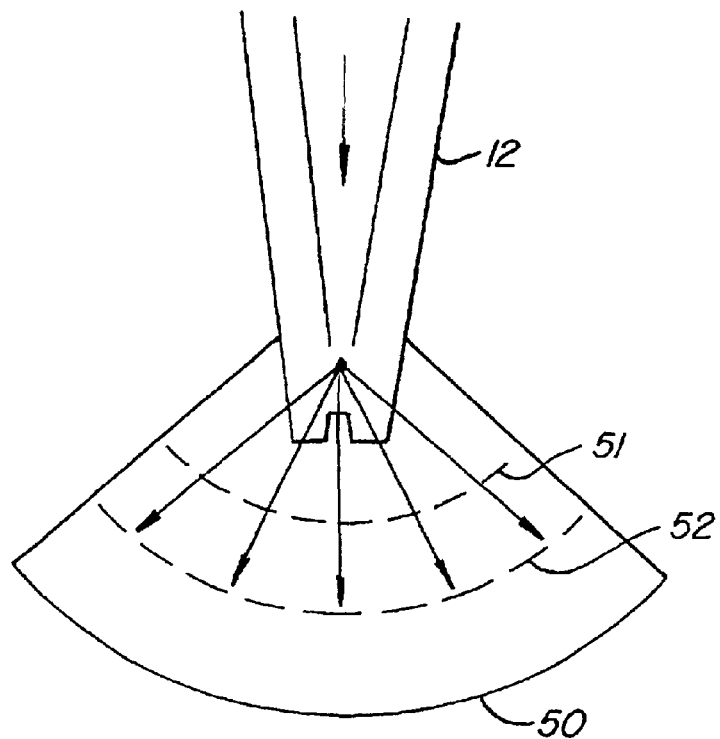

Referring to FIG. 6B, a solid angle of ejection 50 is shown having approximately one pi steradians. In this case, mixed molding compound expands through first expansion front 51 and second expansion front 52 from exit extension 12. This type of ejection is not preferred.

FIGS. 7A and 7B illustrate the use of appliance of the present invention on the lower right jaw of a patient, the illustration being highly schematic. The teeth shown along jaw 60 are the canine 61, first premolar 62, second premolar 63, first molar 64 and second molar 65. Second premolar 63 and first molar 64 are shown having respective preparations 66 and 68 surrounded by respective margins 67 and 69. Intra-oral tip T is shown ejecting mixed molding compound between second premolar 63 and first molar 64. It is common that oral tooth decay occur in the side-by-side teeth. This occurrence creates somewhat complicated placement of the molding compound. Referring to FIG. 7B, movement of intra-oral tip T is shown around first molar 64. Vectors of ejection along the hemispherical front illustrated in FIG. 6A are shown. It can immediately be understood that constant reorientation of the apparatus illustrated in FIG. 1 is not required. Further, and most important, as has been shown in FIG. 7B, there is always a vector of the mixed molding compound ejection which is normal to either the preparation 68 or the margin 69 of first molar 64. Further, by traversing tip T through the preparation 68, delivery of the mixed molding compound to the preparation will be substantially normal to the preparation surfaces.

The reader should understand that the altered molding tip of the present invention does not always ensure normal incidence of molding compound to tooth preparation and margin surfaces. It does, however, create a much higher probability that such normal incidence will occur at at least one part of the preferred hemispherical ejecting profile. Further, it eliminates the need for the constant reorientation of intra-oral tip T referred to above.

What is claimed is:

1. In combination with an apparatus for mixing dental molding compound, an ejection tip comprising in combination:

an ejection tip for attachment to the apparatus for mixing dental molding compound at one end, having an aperture for ejecting molding compound at the other end, and a conduit within the tip for directing mixed molding compound between the apparatus for mixing dental molding compound and the aperture of the ejection tip; and, a nozzle in the ejection tip at the aperture for ejecting molding compound in a uniformly advancing solid angle in the range of at least one pi steradian.

2. The combination with an apparatus for mixing dental molding compound, including the ejection tip of claim 1 wherein:

the nozzle in the ejection tip at the aperture for ejecting molding compound in a uniformly advancing solid angle in the range of at least two pi steradians.

3. The combination with an apparatus for mixing dental molding compound, including the ejection tip of claim 2 wherein:

the nozzle in the ejection tip that the aperture for ejecting molding compound in a uniformly advancing solid angle exceeds two pi steradians.

4. In combination with an apparatus for mixing dental molding compound, an ejection tip comprising:

an ejection tip for attachment to the apparatus for mixing dental molding compound at one end, having an aperture for ejecting molding compound at the other end, and a conduit within the tip for directing mixed molding compound between the apparatus for mixing the dental molding compound and the aperture of the ejection tip, the conduit defining at the aperture of the ejection tip a normal axis of molding compound ejection;

at least three slits at approximately equal angular intervals within the sidewalls of the ejection tip adjacent the aperture for ejecting molding compound whereby the at least three slits in combination with the aperture for ejecting molding compound produce a uniformly advancing solid angle of the ejected molding compound.

5. The combination with an apparatus for mixing dental molding compound, the ejection tip according to claim 4 further comprising:

at least four slits at approximately equal angular intervals.

6. A process for applying molding compound to a tooth having undergone dental surgery sufficient to provide the tooth with a preparation, a margin around the preparation, and adjacent mouth structure including adjacent teeth and gums, the process comprising the steps of:

providing a tooth with the preparation having a surrounding margin with gum structure adjacent to margin;

preparing the tooth with the preparation to receive molding compound;

providing an apparatus for mixing dental molding compound including in the ejection tip having attachment to apparatus for mixing the molding compound at one end, an aperture for the ejection of molding compound at the other end, and a conduit between the attachment and aperture for passing mixed molding compound to and out the aperture for the ejection of molding compound;

placing a nozzle in the ejection tip at the aperture for ejecting molding compound in a uniformly advancing solid angle in the range of at least one pi steradian; and, moving the nozzle in the ejection tip over the tooth at the preparation and margin while ejecting molding compound to produce wetting of the preparation and margin of the tooth by the molding compound.

7. The process for applying molding compound according to claim 6 and wherein the step of placing a nozzle in the ejection tip includes providing a nozzle for ejecting molding compound in a uniformly advancing solid angle in the range of at least two pi steradians.

* * * * *